(12) United States Patent
Lang et al.

(10) Patent No.: US 7,814,914 B2
(45) Date of Patent: Oct. 19, 2010

(54) DEVICE FOR PREVENTING LEAKAGE FROM THE MOUTH

(75) Inventors: Bernd Christoph Lang, Gräfelfing (DE); Achim Biener, Aufkirchen (DE); Martin Bechtel, Winsen/Luhe (DE)

(73) Assignee: MAP Medizin-Technologie GmbH, Martinsried (DE)

( * ) Notice: Subject to any disclaimer, the term of this patent is extended or adjusted under 35 U.S.C. 154(b) by 0 days.

(21) Appl. No.: 11/794,178

(22) PCT Filed: Dec. 30, 2005

(86) PCT No.: PCT/EP2005/014142
§ 371 (c)(1),
(2), (4) Date: Jul. 26, 2007

(87) PCT Pub. No.: WO2006/072454
PCT Pub. Date: Jul. 13, 2006

(65) Prior Publication Data
US 2008/0072916 A1  Mar. 27, 2008

(30) Foreign Application Priority Data
Jan. 3, 2005 (DE) .................. 10 2005 000 712

(51) Int. Cl.
*A61C 5/14* (2006.01)
*A61C 3/00* (2006.01)

(52) U.S. Cl. ..................... 128/859; 128/861; 433/6

(58) Field of Classification Search .......... 128/859, 128/860, 861, 862, 863, 857, 848, 885, 884, 128/837, 834; 27/1, 21.1; 600/32, 29; 606/153, 606/155–157, 234
See application file for complete search history.

(56) References Cited

U.S. PATENT DOCUMENTS

| 6,514,176 | B1 * | 2/2003 | Norton .................. 482/11 |
| 7,153,237 | B2 * | 12/2006 | Norton .................. 482/11 |
| 2002/0069872 | A1 * | 6/2002 | Gradon et al. ......... 128/201.26 |
| 2002/0144685 | A1 | 10/2002 | Ivanovich et al. |
| 2003/0121520 | A1 | 7/2003 | Parker et al. |

FOREIGN PATENT DOCUMENTS

| DE | 743 034 | 1/1944 |
| DE | 25 17 445 | 10/1976 |
| WO | 02/32486 | 4/2002 |
| WO | 2004/052438 | 6/2004 |

OTHER PUBLICATIONS

International Search Report for PCT/EP2005/014142 mailed Feb. 10, 2006.

* cited by examiner

*Primary Examiner*—Patricia M Bianco
*Assistant Examiner*—Ophelia Hawthorne
(74) *Attorney, Agent, or Firm*—Nixon & Vanderhye P.C.

(57) ABSTRACT

The present invention relates to a device for avoiding leakage from the mouth when nasally supplying a respiratory gas on a pressure level lying above ambient pressure. The device comprises a base body made from an elastomeric material and comprises an inner edge portion and an outer ring edge portion, wherein the two ring edge portions are coupled with each other via a web portion, and wherein furthermore the base body, in combination with the two ring edge portions and the web portion, is configured in such a manner that in the application position of the base body the latter defines a lip receiving area for receiving the lips of the user.

12 Claims, 2 Drawing Sheets

DEVICE FOR PREVENTING LEAKAGE FROM THE MOUTH

This application is the US national phase of international application PCT/EP2005/014142 filed 30 Dec. 2005, which designated the U.S. and claims the benefit of German Application No. 10 2005 000 712.0 filed 3 Jan. 2005, each incorporated herein by reference in its entirety.

BACKGROUND OF THE INVENTION

The present invention relates to a device for preventing leakage from the mouth when supplying a respiratory gas on a pressure level which lies above ambient pressure.

In particular for the treatment of sleep-related respiratory diseases it is known to supply a patient with a breathable gas, e.g. ambient air, on a pressure level which lies above ambient pressure at least in phases. It is thus possible to cause an effect in the area of the upper respiratory passages which is called pneumatic splinting and which can prevent possible obstructions in this area. The supply of a breathable gas on a level lying above ambient pressure can also have further therapeutic advantages in addition to the treatment of sleep-related respiratory disorders or disturbances.

In known systems for the treatment of sleep-related respiratory disorders or for supplying a breathable gas on a level lying above ambient pressure, the respiratory gas is normally supplied by means of a supply device, in particular a CPAP device, which is coupled with the respiratory passages of the patient via a flexible respiratory gas conduit and a breathing mask applied to the patient. The breathing mask can be configured in such a manner that the respiratory gas is supplied only nasally or nasally combined with orally. The combined nasal/oral supply of the respiratory gas has proved advantageous vis-à-vis a merely nasal supply of the respiratory gas because in said combined supply no inadmissible leakage from the mouth (flow-off of respiratory gas) can occur.

Although breathing mask systems for the combined nasal/oral supply of the respiratory gas are advantageous in view of the prevention of leakage from the mouth, the users often accept such systems only very reluctantly.

SUMMARY OF THE INVENTION

One aspect of the present invention is to provide solutions which are advantageous in view of a reduced occurrence of leakage from the mouth when supplying a respiratory gas on a pressure level lying above ambient pressure.

In accordance with the present invention, this object is achieved with a device for suppressing leakage from the mouth when nasally supplying a respiratory gas on a pressure level lying above ambient pressure. Said device comprises a base body made from an elastomeric material and having an inner ring edge portion and an outer ring edge portion, wherein the two ring edge portions are coupled with each other via a web portion and wherein moreover the base body, in combination with the two ring edge portions and the web portion, is configured in such a manner that in the application position of the base body the latter defines a lip receiving area for receiving the lips of the user.

Preferably at least one of the ring edge portions is configured so as to be upendable, so that said ring edge portion can be brought from a first position providing an enlarged lip receiving space into a holding position in which there is a reduced space between the two ring edge portions. Upendability can be achieved in that the respective ring edge portion has a convex or concave shape so that the respective position is obtained thereby leading to a temporary deformation, in particular widening of the outer areas and upsetting of the inner areas of the ring edge portion.

The base body is preferably made from a silicone rubber, in particular a fully transparent silicone rubber material.

It is possible to provide the device, in particular the base body, with a lift-off means, e.g., in the form of a ring clip or loop, for facilitating the removal of the base body from the mouth of the user. It is thus possible to remove the device quickly, e.g., for respiration through the mouth. It is possible to configure the lift-off means in such a manner that upon application of tensile forces said lift-off means deforms at least one of the ring edge portions such that the device according to the present invention can be removed easily.

The side of the base body which faces the row of teeth in the application position can be provided with an inner web or any other inner structure for supporting, holding or positioning the base body in combination with the teeth or rows of teeth of the user.

The base body, in particular the ring edge portions thereof, are preferably shaped in such a manner that the lips of the user are slightly clamped in an edge portion that is radially further spaced from the mouth opening by an elastic deformation of the base body. It is thus possible to slightly clamp the lips of the user in an area which surrounds the mouth opening and is less pressure-sensitive.

The outer ring edge portion is preferably configured such that it defines an essentially elliptic and concavely bulged lip rest surface. This means that the shape of the outer ring edge portion preferably corresponds to the shape of the top or cover of a commercially available baby dummy.

The base body can preferably consist of several parts. It is possible to provide different variants of the ring edge portions and to select and combine them in accordance with the requirements of the individual users. It is also possible to shape the device according to the present invention specifically for an individual user, for example by making impressions of the open mouth.

Furthermore, a channel means via which the respiratory gas is supplied and discharged in a defined manner can be provided in the area of the web portion. It is possible to assign to said channel means a valve or throttle arrangement which allows, e.g., the inspiration of air or a limited expiration of air. It is possible to supply said channel means via a connecting conduit which communicates, e.g., with the overpressure region of the mask. It is also possible to control the throttle or valve means depending on the nasally applied respiratory gas pressure.

BRIEF DESCRIPTION OF THE DRAWINGS

Further details and features of the invention can be taken from the following description in combination with the drawings in which.

DETAILED DESCRIPTION OF EXAMPLE EMBODIMENTS

Figure 1:
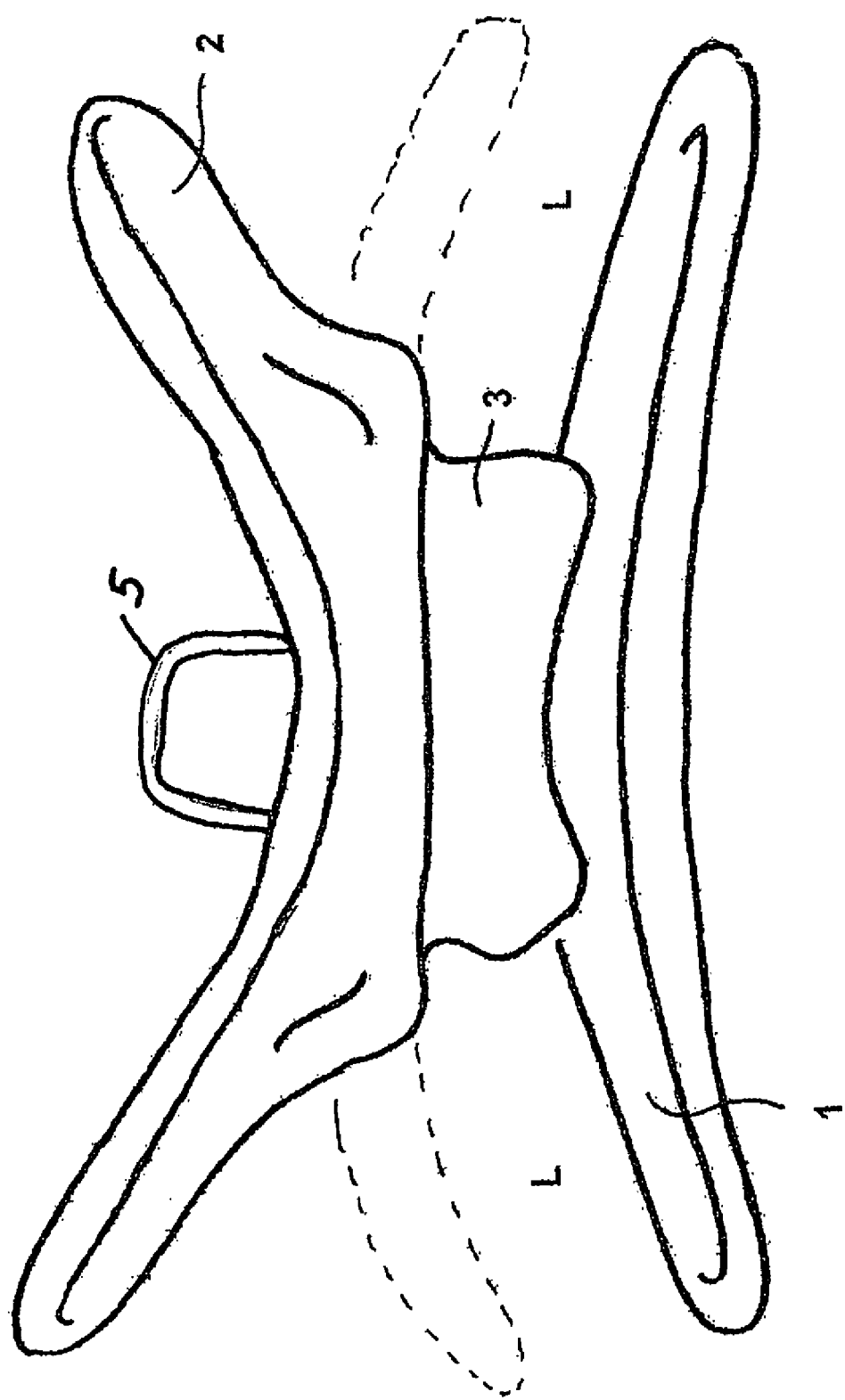
FIG. 1 is a sketch for explaining a preferred configuration of the device according to the present invention.

The device shown in FIG. 1 serves for suppressing leakage from the mouth when nasally supplying a respiratory gas on a pressure level lying above ambient pressure.

The device comprises a base body made from an elastomeric material. The base body in turn comprises an inner ring edge portion 1 and an outer ring edge portion 2. The two ring edge portions 1, 2 are coupled with each other via a web or joining portion 3. The base body, in combination with the two ring edge portions 1, 2 and the web portion 3, is configured in such a manner that in the application position of the base body the latter defines a lip receiving area L for receiving the lips of the user.

In the shown embodiment, the outer ring edge portion 2 is upendable, i.e. bulgeable so as to snap-in, so that the outer ring edge portion 2 can be brought from a first position (shown) providing an enlarged lip receiving area L into a holding position (dashed lines) in which a reduced gap between the two ring edge portions 1, 2 is formed.

The base body is made from a silicone rubber and provided with a lift-off device 5, which can be realized, e.g., as a ring bracket, for facilitating the removal of the base body from the mouth of the user.

The base body can be realized in such a manner that the ring edge portions are shaped such that the lips of the user are slightly clamped in an edge portion that is radially further spaced from the mouth opening by an elastic deformation of the base body.

The outer ring edge portion 2 can furthermore be configured such that the latter defines an essentially polygonally or elliptically contoured lip rest area which is concavely bulged towards the user.

Figure 2B:
FIG. 2b is a sketch for explaining how a further variant of the device according to the present invention is seated in the mouth area of a user.
Figure 2A:
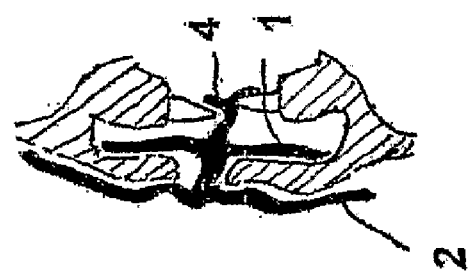
FIG. 2a is a sketch for explaining how the device according to the present invention is seated in the mouth area of a user.

The device according to one aspect of the present invention can be configured in such a manner that it cooperates with the lips of the user in the application position shown in FIG. 2a. In this example, the outer ring edge portion 2 is configured such that it projects from the inner ring edge portion 1 in the radial direction. As an example only, this embodiment also shows a web projection or inner web 4 which projects into the gap between the teeth rows and which allows a further positioning of the device over the mouth area of the user.

FIG. 2b shows a variant in which the outer ring edge portion 2, the web portion 3 and the inner ring edge portion 1 are configured such that the inner ring edge portion 1 rests on an inner side of the rows of teeth facing away from the lips of the user.

Figure 3:
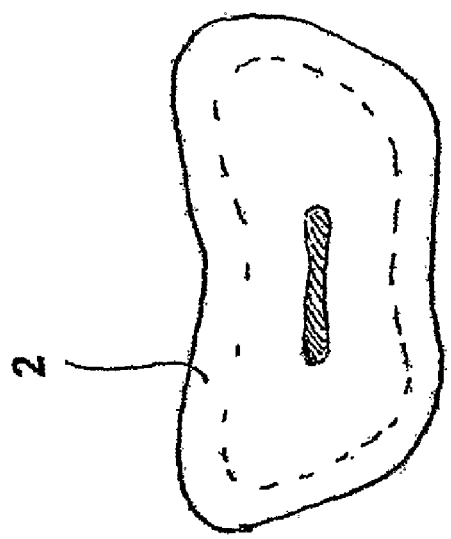
FIG. 3 is a sketch for explaining how the outer ring edge portion as well as the cross-section of the web portion can possibly be contoured.

FIG. 3 shows a preferred polygonal Contouring of the outer ring edge portion 2. The outer ring edge portion 2 preferably forms a rest area which is concavely bulged towards the user and whose bulging preferably essentially corresponds to a large extent to the bulging of the area surrounding the mouth. The outer ring edge portion 2 is contoured such that it is slightly recessed in the rest area of the upper lip, close to the opening of the nose, as well as diametrically opposite thereof. Said contouring is preferably selected such that the outer ring edge portion has a favorable feathering outer edge.

As seen in FIGS. 1-3, especially the cross-sections of FIGS. 2a and 2b, the base body is a solid member which is dimensioned to cover the opening of the mouth in use and which does not include an aperture.

The invention claimed is:

1. A device for suppressing leakage from the mouth when nasally supplying a respiratory gas on a pressure level lying above ambient pressure, the device comprising:
a base body made from an elastomeric material and comprising an inner ring edge portion and an outer ring edge portion, wherein the two ring edge portions are coupled with each other via a joining portion and wherein furthermore the base body, in combination with the two ring edge portions as well as the joining portion, are configured in such a manner that in the application position of the base body the base body defines a lip receiving area adapted for receiving the lips of the user while suppressing leakage from the mouth, wherein the outer ring edge portion extends radially outward beyond the inner ring edge portion in the application position, wherein the base body comprises a solid member dimensioned to cover the opening of the mouth in use.

2. The device according to claim 1, wherein at least one of the ring edge portions is upendable so that it can be brought from a first position providing an enlarged lip receiving area into a holding position in which a reduced gap between the two ring edge portions is formed.

3. The device according to claim 1, wherein the base body is made from a silicone rubber.

4. The device according to claim 1, wherein the base body is configured in such a manner that the ring edge portions are adapted and shaped to slightly clamp the lips of the user in an edge portion that is radially further spaced from the mouth opening by an elastic deformation of the base body.

5. A device for suppressing leakage from the mouth when nasally supplying a respiratory gas on a pressure level lying above ambient pressure, the device comprising:
a base body made from an elastomeric material and comprising an inner ring edge portion and an outer ring edge portion, wherein the two ring edge portions are coupled with each other via a joining portion and wherein furthermore the base body, in combination with the two ring edge portions as well as the joining portion, are configured in such a manner that in the application position of the base body the base body defines a lip receiving area adapted for receiving the lips of the user while suppressing leakage from the mouth, further comprising a lift-off device provided to facilitate the removal of the base body from the mouth of the user, the lift off device being structured to deform the outer ring edge portion upon application of tensile forces to the lift-off device, wherein the base body comprises a solid member dimensioned to cover the opening of the mouth in use.

6. The device according to claim 5, wherein the lift-off device comprises a ring clip, a loop or a ring bracket.

7. A device for suppressing leakage from the mouth when nasally supplying a respiratory gas on a pressure level lying above ambient pressure, the device comprising:
a base body made from an elastomeric material and comprising an inner ring edge portion and an outer ring edge portion, wherein the two ring edge portions are coupled with each other via a joining portion and wherein furthermore the base body, in combination with the two ring edge portions as well as the joining portion, are configured in such a manner that in the application position of the base body the base body defines a lip receiving area adapted for receiving the lips of the user, at least said outer ring edge portion being solid so as to suppress suppressing leakage from the mouth, wherein the base body is provided with an inner web adapted to extend and to be anchored behind the user's teeth, wherein the base body comprises a solid member dimensioned to cover the opening of the mouth in use.

8. A device for suppressing leakage from the mouth when nasally supplying a respiratory gas on a pressure level lying above ambient pressure, the device comprising:

a base body made from an elastomeric material and comprising an inner ring edge portion and an outer ring edge portion, wherein the two ring edge portions are coupled with each other via a joining portion and wherein furthermore the base body, in combination with the two ring edge portions as well as the joining portion, are configured in such a manner that in the application position of the base body the base body defines a lip receiving area adapted for receiving the lips of the user while suppressing leakage from the mouth, wherein the outer ring edge portion is configured such that it defines an essentially elliptically and concavely bulged lip rest area, wherein the base body comprises a solid member dimensioned to cover the opening of the mouth in use.

9. A device for suppressing leakage from the mouth when nasally supplying a respiratory gas on a pressure level lying above ambient pressure, the device comprising:

a base body made from an elastomeric material and comprising an inner ring edge portion and an outer ring edge portion, wherein the two ring edge portions are coupled with each other via a joining portion and wherein furthermore the base body, in combination with the two ring edge portions as well as the joining portion, are configured in such a manner that in the application position of the base body the base body defines a lip receiving area adapted for receiving the lips of the user while suppressing leakage from the mouth, wherein the outer ring edge portion extends radially outward beyond the inner ring edge portion in the application position, wherein the base body does not include an aperture.

10. A device for suppressing leakage from the mouth when nasally supplying a respiratory gas on a pressure level lying above ambient pressure, the device comprising:

a base body made from an elastomeric material and comprising an inner ring edge portion and an outer ring edge portion, wherein the two ring edge portions are coupled with each other via a joining portion and wherein furthermore the base body, in combination with the two ring edge portions as well as the joining portion, are configured in such a manner that in the application position of the base body the base body defines a lip receiving area adapted for receiving the lips of the user while suppressing leakage from the mouth, further comprising a lift-off device provided to facilitate the removal of the base body from the mouth of the user, the lift off device being structured to deform the outer ring edge portion upon application of tensile forces to the lift-off device, wherein the base body does not include an aperture.

11. A device for suppressing leakage from the mouth when nasally supplying a respiratory gas on a pressure level lying above ambient pressure, the device comprising:

a base body made from an elastomeric material and comprising an inner ring edge portion and an outer ring edge portion, wherein the two ring edge portions are coupled with each other via a joining portion and wherein furthermore the base body, in combination with the two ring edge portions as well as the joining portion, are configured in such a manner that in the application position of the base body the base body defines a lip receiving area adapted for receiving the lips of the user, at least said outer ring edge portion being solid so as to suppress suppressing leakage from the mouth, wherein the base body is provided with an inner web adapted to extend and to be anchored behind the user's teeth, wherein the base body does not include an aperture.

12. A device for suppressing leakage from the mouth when nasally supplying a respiratory gas on a pressure level lying above ambient pressure, the device comprising:

a base body made from an elastomeric material and comprising an inner ring edge portion and an outer ring edge portion, wherein the two ring edge portions are coupled with each other via a joining portion and wherein furthermore the base body, in combination with the two ring edge portions as well as the joining portion, are configured in such a manner that in the application position of the base body the base body defines a lip receiving area adapted for receiving the lips of the user while suppressing leakage from the mouth, wherein the outer ring edge portion is configured such that it defines an essentially elliptically and concavely bulged lip rest area, wherein the base body does not include an aperture so as to completely suppress leak through the base body.

* * * * *